United States Patent [19]  [11]  4,138,566
Krimmel  [45] * Feb. 6, 1979

[54] PIPERAZINYL CYCLOBUTENONES
[75] Inventor: Carl P. Krimmel, Wauconda, Ill.
[73] Assignee: G. D. Searle & Co., Chicago, Ill.
[*] Notice: The portion of the term of this patent subsequent to Sep. 27, 1994, has been disclaimed.
[21] Appl. No.: 810,347
[22] Filed: Jun. 27, 1977

Related U.S. Application Data

[63] Continuation-in-part of Ser. No. 674,519, Apr. 7, 1976, Pat. No. 4,051,136.
[51] Int. Cl.$^2$ .................. C07D 241/06; C07D 241/12
[52] U.S. Cl. ..................................... 544/357; 424/250
[58] Field of Search ..................... 260/268 B; 544/357

[56]  References Cited

U.S. PATENT DOCUMENTS 4,051,136  9/1977  Krimmel .......................... 260/268 R Primary Examiner—Jose Tovar
Attorney, Agent, or Firm—John J. Kolano; Joy A. Serauskas

[57]  ABSTRACT

1-[2-Hydroxy-3-(4-alkyl-1-piperazinyl)-4-oxo-2-cyclobuten-1-ylidene]-4-alkylpiperazinium hydroxide inner salts and related compounds are described herein. These compounds are useful as anti-viral agents. They are prepared from 2-anilino-3-hydroxy-4-(phenylimino)-2-cyclobuten-1-one and the appropriate monosubstituted piperazine.

4 Claims, No Drawings

PIPERAZINYL CYCLOBUTENONES

The present application is a continuation-in-part of application Ser. No. 674,519, filed Apr. 7, 1976, now U.S. Pat. No. 4,051,136, issued Sept. 27, 1977.

The present invention relates to a group of compounds which are piperazinyl cyclobutenones. More particularly, it relates to a group of compounds having the following general formula.

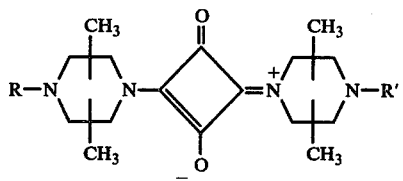

wherein R and R' are alkyl containing from 2 to 6 carbon atoms. It should be noted that the structure given above is one of four equivalent canonical structures that can be written for the compounds of the present invention.

As indicated above, the alkyl groups contain from 2 to 6 carbon atoms. These alkyl groups can be straight chain or branched and are exemplified by ethyl, propyl, isopropyl, butyl, and hexyl.

Equivalent to the above compounds for the purposes of this invention are the pharmaceutically acceptable acid addition salts with a variety of organic and inorganic acids. Such salts are formed with acids such as sulfuric, phosphoric, hydrochloric, hydrobromic, hydroiodic, sulfamic, citric, lactic, maleic, malic, succinic, tartaric, cinnamic, acetic, benzoic, gluconic, ascorbic, and related acids.

The compounds of the present invention are conveniently prepared by the reaction of an appropriate 1-alkylpiperazine with an anilinocyclobutenone having the following formula

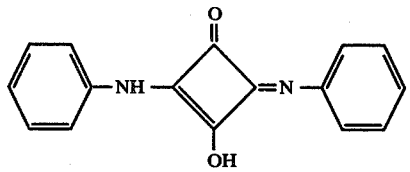

The reaction is carried out neat with heating at about 190–240° C. While the necessary anilinocyclobutenone starting material is known, the procedures for its preparation which appear in the literature give a mixture of isomers. However, it has now been found that, if squaric acid is reacted with aniline using pyridine as the solvent and the product is washed with dimethylformamide, the desired 2,4-isomer is obtained in high purity. Alternatively, it is also possible to obtain the compounds of the present invention by the direct reaction of squaric acid with a 1-alkylpiperazine.

The compounds of the present invention are useful as anti-viral agents. In particular, the present compounds have been found active against influenza A (strain 575) virus and Herpesvirus hominis type 2 strain MS. The present compounds can thus be combined with various known excipients and adjuvants in the form of dusts, solutions, suspensions, ointments and sprays to provide compositions useful for disinfecting purposes, such as for laboratory equipment.

The anti-viral utility of the instant compounds is evident from the results of a standardized test to determine their anti-viral activity. This activity is determined by the following test procedure.

Cell cultures of primary Rhesus monkey kidney maintained in 25 cm$^2$ plastic flasks and each containing test compound at concentrations of 625, 125, 25, 5, or 1 microgram per milliliter are prepared in pairs. These flasks, and an identical pair of flasks containing no test compound, are each inoculated with a dose of influenza virus type A (strain 575) previously shown to produce maximum hemadsorption and minimum cytopathogenic effects after a 24 hour incubation. Where the cultures contain test compound, the virus is added one hour after addition of the compound to the culture. After 24 hours incubation of the cultures, the supernatant fluids are removed and 4.0 ml. of a 0.4% suspension of guinea pig erythrocytes are added to each flask. The flasks are then incubated at 4° C. in a horizontal position for 30 minutes. The flasks are rocked every 10 minutes during the incubation period. After this incubation, the red cell suspension is decanted from each flask, the flasks are washed twice with 4.0 ml. of phosphate buffer saline solution (pH 7.4) to remove unabsorbed red cells, and 4.0 ml. of distilled water is then added to lyse the adsorbed cells. The flasks are then further incubated at 37° C. for 30 minutes in a horizontal position and the flasks are rocked every 10 minutes. After this incubation, the fluid contents of the pairs of flasks are combined to form an essay unit and are placed at room temperature for 15–30 minutes to allow settling of cellular debris. A pair of control flasks identical with the above, except for the absence of test compound and virus inoculation, is run concurrently. The resulting hemoglobin solutions from each essay unit are then read for optical density in a spectrophotometer. A test compound is considered active if, at one of the tested levels, it reduces the optical density reading by at least 50% relative to the virus control. The optical densities observed are further used to calculate the concentration of test compound which would produce a 50% reduction in the optical density reading. When 1-[2-hydroxy-3-(cis-3,5-dimethyl-4-propyl-1-piperazinyl)-4-oxo-2-cyclobuten-1-ylidene]-cis-3,5-dimethyl-4-propylpiperazinium hydroxide inner salt and 1-[2-hydroxy-3-(cis-2,6-dimethyl-4-propyl-1-piperazinyl)-4-oxo-2-cyclobuten-1-ylidene]-cis-2,6-dimethyl-4-propylpiperazinium hydroxide inner salt were tested by the above procedure, they were found to be active as anti-viral agents.

A further test demonstrating the anti-viral utility of the present compounds is as follows: The test compound is dissolved in water or a suitable organic solvent. One-quarter inch filter paper discs are each impregnated with 200 μg. of a test compound contained in 0.02 ml. of solution and allowed to dry. Monolayer cell cultures of primary rabbit kidney are established in multidish plates, each plate consisting of 6×34 mm. wells. After cell outgrowth, the nutrient fluids are removed from the wells and the cell sheets are inoculated with 0.25 ml. of a dilution of Herpes virus hominis type 2 strain MS previously shown to cause confluent lysis of the cell sheets. After the virus adsorption period, the inoculum is removed by aspiration, and 2.0 ml. of an agar overlay containing neutral red is added and allowed to solidify. The one-quarter inch filter paper discs previously impregnated with the test compound are then placed onto the center of the agar surface of each well. The plates are incubated at 37° C. for four days, at the end of which time they are examined for zones of cytotoxicity and antiviral inhibition. A ratio is then determined for the diameter of the antiviral zone versus the diameter of the cytotoxic zone. A representative compound of this invention which shows activity in this test is 1-[2-hydroxy-3-(cis-3,5-dimethyl-4-ethyl)-1-piperazinyl)-4-oxo-2-cyclobuten-1-ylidene]-cis-3,5-dimethyl-4-ethylpiperazinium hydroxide inner salt.

Those skilled in the art will recognize that observations of activity and standardized tests for particular biological effects are fundamental to the development of valuable drugs, both veterinary and human.

The following examples are presented to further illustrate the present invention. They should not be construed as limiting it in spirit or in scope. In these examples, temperatures are indicated in degrees centigrade (° C.), quantities by weight are indicated in grams and quantities by volume are indicated in mililiters.

EXAMPLE 1

To a solution of 50 grams of cis-2,6-dimethylpiperazine in 130 ml. of water and containing bromphenol blue as indicator, there is added, with stirring and cooling, a solution of 100 ml. of concentrated hydrochloric acid in 500 ml. of water until the bromphenol blue just turns yellow. Then, 47.7 grams of ethyl chloroformate is introduced in 5 ml. portions by rapid, dropwise addition with stirring. After each 5 ml. addition, aqueous 25% sodium hydroxide solution is added dropwise until the indicator turns green. The addition of reactants is continued until thin layer chromatography shows that all of the piperazine has reacted. The reaction mixture is then made alkaline with aqueous 50% sodium hydroxide solution and then extracted with ethyl ether. The combined ether extracts are dried over anhydrous sodium sulfate and then chromatographed on a low pressure silica gel column using a mixture of 2% ethanol, 0.25% concentrated ammonium hydroxide and 97.75% methylene chloride to apply the reaction mixture to the column. Fractions are collected from the column by elution with this solvent and the solvent is evaporated to leave pure 1-ethoxycarbonyl-cis-3,5-dimethylpiperazine. The column is further eluted with a mixture of 5% ethanol, 0.25% concentrated ammonium hydroxide and 94.75% methylene chloride and the solvent is evaporated from the fractions collected to leave a residue which is 1-ethoxycarbonyl-cis-2,6-dimethylpiperazine.

EXAMPLE 2

A mixture of 25.8 grams of 1-ethoxycarbonyl-cis-3,5-dimethylpiperazine, 38.6 grams of propyl 4-toluene-sulfonate, 90 ml. of absolute ethanol and 9.5 grams of sodium carbonate is stirred and heated to reflux. After 30 minutes of reflux, vigorous evolution of carbon dioxide begins and continues for about 5 hours. Refluxing is continued for a total of 22 hours. The reaction mixture is then cooled and filtered and the solvent is evaporated. The resulting residue is mixed with 300 ml. of aqueous 1 N sodium hydroxide solution and the mixture is extracted with ethyl ether. The ether extract is washed successively with 100 ml. of aqueous 1 N sodium hydroxide and 100 ml. of water and then dried over anhydrous sodium sulfate. The organic solution is then treated with charcoal and the solvent is evaporated to leave a residue which is purified by chromatography to give 4-ethoxycarbonyl-cis-2,6-dimethyl-1-propylpiperazine. If 1-ethoxycarbonyl-cis-2,6-dimethylpiperazine is reacted with propyl 4-toluenesulfonate according to this same procedure, the product obtained is 1-ethoxycarbonyl-cis-2,6-dimethyl-4-propylpiperazine.

EXAMPLE 3

A mixture of 11 grams of 4-ethoxycarbonyl-cis-2,6-dimethyl-1-propylpiperazine and 150 ml. of concentrated hydrochloric acid is refluxed for 26 hours. The reaction mixture is then cooled and made alkaline by the cautious addition of aqueous 50% potassium carbonate solution. Solid potassium carbonate is then added until a white flocculent precipitate forms. The resulting mixture is extracted with ether and the ether extract is treated with activated carbon and dried over anhydrous sodium sulfate. Evaporation of the solvent on a steam bath under nitrogen leaves a pale orange-brown liquid which is pure cis-2,6-dimethyl-1-propylpiperazine as shown by thin layer chromatography. If 1-ethoxycarbonyl-cis-2,6-dimethyl-4-propylpiperazine is treated with concentrated hydrochloric acid according to the procedure described above the product obtained is cis-3,5-dimethyl-1-propylpiperazine.

EXAMPLE 4

A mixture of 9.0 grams of 1-ethoxycarbonyl-cis-3,5-dimethylpiperazine, 14.6 grams of ethyl 4-toluenesulfonate, 50 ml. of absolute ethanol, and 3.9 grams of sodium carbonate is stirred and refluxed for 18 hours. The reaction mixture is than cooled and filtered and the solvent is evaporated from the filtrate. The residue is dissolved in 30 ml. of water and the resulting aqueous solution is extracted with one 100 ml. and one 50 ml. portion of anhydrous ethyl ether. The ether extracts are combined, washed with 10 ml. of water, and dried over anhydrous sodium sulfate. The ether is then evaporated from the solution on a steam bath under a stream of dry nitrogen to leave a pale yellow liquid which is 4-ethoxycarbonyl-cis-2,6-dimethyl-1-ethylpiperazine.

A mixture of 9.2 grams of 4-ethoxycarbonyl-cis-2,6-dimethyl-1-ethylpiperazine and 30 ml. of concentrated hydrochloric acid is stirred and refluxed for 24 hours. The reaction mixture is then carefully treated with solid potassium carbonate until the solution is saturated. It is then extracted with 200 ml. of anhydrous ethyl ether and the ether extract is dried over anhydrous sodium sulfate. Evaporation of the solvent under a vacuum and using a stream of dry nitrogen gives a yellow oil which is cis-2,6-dimethyl-1-ethylpiperazine.

EXAMPLE 5

A mixture of 1.5 grams of 2-anilino-3-hydroxy-4-(phenylimino)-2-cyclobuten-1-one and 1.2 grams of cis-2,6-dimethyl-1-ethylpiperazine is heated at 213° C. in an atmosphere of dry nitrogen for 10 minutes. It is then mixed thoroughly with 25 ml. of anhydrous ethyl ether and suction filtered and this process is repeated. The solid is then dissolved in 200 ml. of anhydrous ethyl ether at room temperature by stirring for 10 minutes. The solution is then stirred with activated charcoal, filtered, and concentrated to a volume of 25 ml. The solid which forms is separated by filtration to give 1-[2-hydroxy-3-(cis-3,5-dimethyl-4-ethyl-1-piperazinyl)-4-oxo-2-cyclobuten-1-ylidene]-cis-3,5-dimethyl-4-ethylpiperazinium hydroxide inner salt as pale pink crystals melting at about 178°–181° C.

EXAMPLE 6

A mixture of 1.5 grams of 2-anilino-3-hydroxy-4-(phenylimino)-2-cyclobuten-1-one and 1.9 grams of cis-2,6-dimethyl-1-propylpiperazine is heated at 216°-218° C. for 15 minutes under an atmosphere of dry nitrogen. The product is then isolated as described in Example 5 to give 1-[2-hydroxy-3-(cis-3,5-dimethyl-4-propyl-1-piperazinyl)-4-oxo-2-cyclobuten-1-ylidene]-cis-3,5-dimethyl-4-propylpiperazinium hydroxide inner salt as a pale pinkish brown microcrystalline solid melting at about 202°-204° C.

EXAMPLE 7

A mixture of 0.48 grams of 2-anilino-3-hydroxy-4-(phenylimino)-2-cyclobuten-1-one and 0.63 grams of cis-3,5-dimethyl-1-propylpiperazine is heated at 230°-240° C. for 10 minutes. The product is then isolated from the reaction mixture according to the procedure described in Example 5 to give 1-[2-hydroxy-3-(cis-2,6-dimethyl-4-propyl-1-piperazinyl)-4-oxo-2-cyclobuten-1-ylidene]-cis-2,6-dimethyl-4-propyl-piperazinium hydroxide inner salt melting at about 218°-227° C. This compound has the following formula

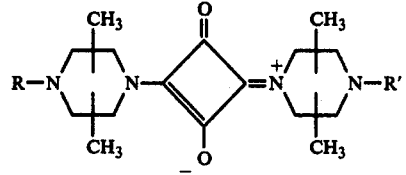

What is claimed is:

1. A compound of the formula wherein R and R' are alkyl having from 2 to 6 carbon atoms.

2. A compound according to claim 1 which is 1-[2-hydroxy-3-(cis-3,5-dimethyl-4-ethyl-1-piperazinyl)-4-oxo-2-cyclobuten-1-ylidene]-cis-3,5-dimethyl-4-ethyl-piperazinium hydroxide inner salt.

3. A compound according to claim 1 which is 1-[2-hydroxy-3-(cis-3,5-dimethyl-4-propyl-1-piperazinyl)-4-oxo-2-cyclobuten-1-ylidene]-cis-3,5-dimethyl-4-propyl-piperazinium hydroxide inner salt.

4. A compound according to claim 1 which is 1-[2-hydroxy-3-(cis-2,6-dimethyl-4-propyl-1-piperazinyl)-4-oxo-2-cyclobuten-1-ylidene]-cis-2,6-dimethyl-4-propyl-piperazinium hydroxide inner salts.